(12) United States Patent  (10) Patent No.: US 7,118,877 B2
Edris  (45) Date of Patent: Oct. 10, 2006

(54) CASPASE 9 ACTIVATION AND USES THEREFOR

(75) Inventor: Wade Allen Edris, New Hope, PA (US)

(73) Assignee: Wyeth, Madison, NJ (US)

( * ) Notice: Subject to any disclaimer, the term of this patent is extended or adjusted under 35 U.S.C. 154(b) by 250 days.

(21) Appl. No.: 10/191,254

(22) Filed: Jul. 8, 2002

(65) Prior Publication Data

US 2004/0005650 A1    Jan. 8, 2004

(51) Int. Cl.
  *G01N 33/52* (2006.01)
  *C12Q 1/37* (2006.01)
  *C12N 9/50* (2006.01)
  *A61K 38/48* (2006.01)
  *A61K 38/07* (2006.01)
(52) U.S. Cl. .................. 435/7.6; 435/24; 435/212; 424/94.63; 514/18
(58) Field of Classification Search ............... 435/7.6, 435/24, 212; 424/94.63; 514/18
  See application file for complete search history.

(56) References Cited

U.S. PATENT DOCUMENTS

| | | | |
|---|---|---|---|
| 6,114,132 A * | 9/2000 | Desmarais et al. ......... | 435/7.6 |
| 6,121,416 A | 9/2000 | Clark et al. | |
| 6,221,355 B1 | 4/2001 | Dowdy | |
| 6,271,361 B1 | 8/2001 | Alnemri et al. | |
| 6,274,318 B1 * | 8/2001 | Alnemri et al. ............... | 435/6 |
| 6,342,611 B1 | 1/2002 | Weber et al. | |
| 6,391,575 B1 * | 5/2002 | Fritz et al. .................. | 435/23 |
| 6,455,296 B1 | 9/2002 | Alnemri | |
| 2001/0016345 A1 | 8/2001 | Alnemri | |

OTHER PUBLICATIONS

Hall et al., "Activation of the Herpes Simplex Virus Type I protease," J Biol Chem 270(39):22697-22700, 1995.*
Renatus et al., "Dimer formation drives the activation of the cell death protease caspase 9," Proc Natl Acad Sci USA 98(25):14250-14255, 2001.*
Principles of Biochemistry, Lehninger, ed., Chap. 16, pp. 441-445, Worth Publishers, Inc., New York, 1982.*
Definitions of peptide and polypeptide, Merriam-Webster Online Dictionary, www.m-w.com, printed from the Internet on Sep. 2, 2004.*
Definition of oligopeptide, MedicineNet.com on-line dictionary, http://www.medterms.com/script/main/hp.asp, printed from the Internet on Sep. 2, 2004.*
Collins, "Sticky ions in biological systems," Proc Natl Acad Sci USA 92:5553-5557, 1995.*
Washabaugh et al., "The systematic characterization by aqueous column chromatography of solutes which affect protein solubility," J Biol Chem 261(27):12477-12485, 1986.*
Jeruzalmi et al. "Use of organic cosmotropic solutes to crystallize flexible proteins: application to T7 RNA polymerase and its complex with the inhibitor T7 lysozyme," J Mol Biol 274:748-756, 1997.*
C.H. Weber and C. Vincenz, "The death domain superfamily: a tale of two interfaces?" *Trends in Biochemical Sciences*, 26(8): 475-481, 2001.
M. Renatus et al. "Dimer formation drives the activation of the cell death protease caspase 9," *PNAS* 98(25): 14250-14255, 2001.

(Continued)

*Primary Examiner*—Robert A. Wax
*Assistant Examiner*—Rosanne Kosson
(74) *Attorney, Agent, or Firm*—Kirkpatrick & Lockhart Nicholson Graham LLP

(57) ABSTRACT

The present invention discloses methods for activating Caspase 9 in such a way that it can be used in assays to discover modulators of Caspase 9.

14 Claims, 17 Drawing Sheets

OTHER PUBLICATIONS

M. Ru et al. "On the salt-induced activation of lyophilized enzymes in organic solvents: Effect of salt kosmotropicity on enzyme activity," *Journal of the American Chemical Society* 122(8): 1565-1571, 2000.

M. Cacace et al. "The Hofmeister series: salt and solvent effects on interfacial phenomena," *Quart. Rev. of Biophysics* 30: 241-277, 1997.

D. Hall and P. Darke. "Activation of the Herpes Simplex virus type 1 protease," *Journal of Biological Chemistry* 270(39): 22697-22700, 1995.

Nicholson et al. "Identification and inhibition of the ICE/CED-3 protease necessary for mammlian apoptosis," *Nature* 376: 37-43, 1995.

*Current Protocols in Cell Biology*, Chapter 18.

G. Smith et al. "Expression, preparation, and high-throughput screening of Caspase-8: discovery of redox-based and steroid diacid inhibition," *Arch. Biochem. Biophys.* 399(2): 195-205, 2002.

Boatright, K. et al., "A Unified Model for Apical Caspase Activation," Molecular Cell, 529-541, Feb.11, 2003, Cell Press.

Collins, "Sticky Ions in Biological Systems," *Proc. Natl. Acad. Sci. USA*, vol. 92, pp. 5553-5557, Jun. 1995.

Schmidt et al., "Dimerization and Activation of the Herpes Simplex Virus Type I Protease," *J. Biol. Chem.*, vol. 272, No. 12, pp. 7732-7735, 1997.

Washabaugh et al., "The Systematic Characterization by Aqueous Column Chromatography of Solutes Which Affect Protein Stability," *J. Biol. Chem.*, vol. 261, No. 27, pp. 12477-12485, 1986.

\* cited by examiner

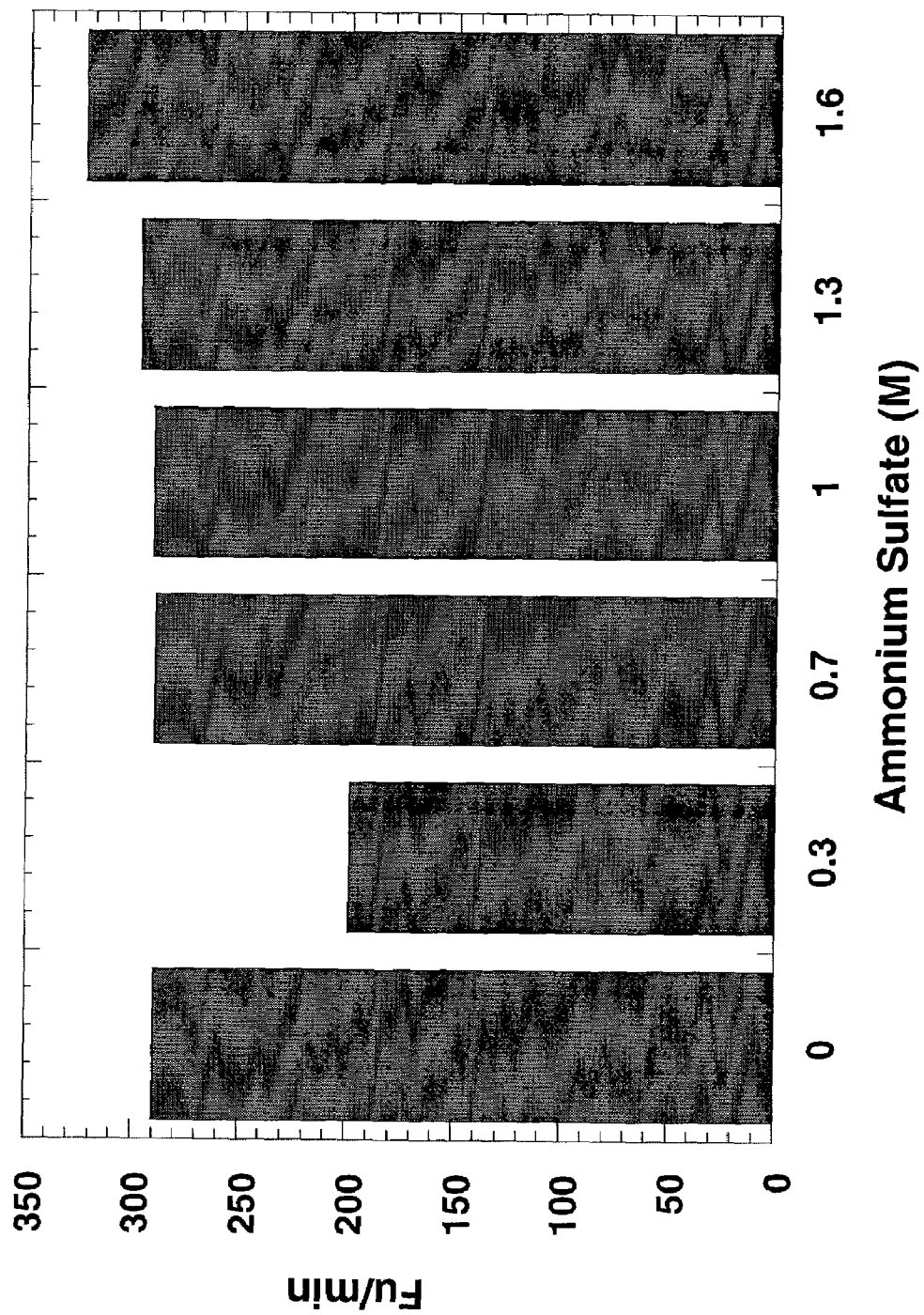

CASPASE 9 ACTIVATION AND USES THEREFOR

FIELD OF THE INVENTION

The present invention relates generally to molecular medicine and drug screening assays and more specifically to interactions involved in regulating programmed cell death and methods of identifying drugs that alter such interactions.

BACKGROUND INFORMATION

Apoptosis, or programmed cell death, is a crucial life-cycle decision point for cells in multicellular organisms from *C. elegans* to humans. It is a vital process in normal embryogenesis and development, maintenance of homeostasis, and immune system function. The regulation and initiation of apoptosis is a complex and intricately regulated process, consistent with this diversity of function. The death domain superfamily has emerged as the prime mediator of the interactions necessary for transducing a death signal. This superfamily consists of death domain (DD), death effector domain (DED) and caspase recruitment domain (CARD) families. Each of these families interacts with other proteins through homotypic interactions in which CARD—CARD, DD—DD and DED—DED contacts are formed exclusively.

Caspases are the primary executioners of apoptosis, with effector caspases cleaving essential proteins such as poly (ADP-ribose) polymerase (PARP), and activating endonucleases such as CAD (by cleavage of the inhibitor ICAD). Upstream caspases, such as Caspases 8 and 9, are activated by signaling complexes such as the death-inducing signaling complex (DISC) and the apoptosome, respectively. Binding of caspases to specific adaptor molecules via CARD or DED domains leads to autoactivation of caspases. For example, the apoptosome consists of Apaf-1, Caspase 9 and cytochrome c and, within this structure, Apaf-1 interacts with proCaspase 9 via a CARD—CARD interaction. Cytochrome c binding to Apaf-1 activates the complex to allow recruitment and autoactivation of proCaspase 9. It is probable that the complex contains multiple Apaf-1 and proCaspase-9 molecules as the active complex has a molecular weight of 700 kDa.

The apoptosome, as well as the Fas DISC and the Pelle-containing complex are examples of large regulatory complexes involved in apoptosis. The proteins in these complexes are composed of multiple domains such as protein—protein interaction motifs, kinase domains, proteolytic domains, ligand-binding domains and membrane-binding domains. The death domains invariably provide one of the means for intramolecular communication. For a review, see C. H. Weber and C. Vincenz, "The death domain superfamily: a tale of two interfaces?" *Trends in Biochemical Sciences*, Vol. 26 No. 8, 2001.

Caspase 9 is a member of the aspartate-specific cysteine protease (ASCP) family of proteases that includes, for example, ICE, CPP32, Nedd2/Ich-1, Mch2, Mch3, Mch4, Mch5, TX (ICH-2, ICErel-III), and ICErel-III.

Caspase 9 shares amino acid sequence homology with several ASCPS, but its catalytic site QACGG differs in the fourth residue from the relatively conserved catalytic sites in other known ACSPs. U.S. Pat. No. 6,271,361, which discloses the DNA and amino acid sequences for Caspase 9, is hereby incorporated by reference in its entirety.

Like many ASCPs, Caspase 9 is synthesized as a proenzyme, which can be proteolytically cleaved by, for example, CPP32 or granzyme B. Cleavage of Caspase 9 yields two subunits, a large subunit and a small subunit, which associate to form an active heterodimer complex. In particular, CPP32 can cleave proCaspase 9 into a large subunit having an approximate molecular weight of 37 kDa (p37) and a small subunit having an approximate molecular weight of 10 kDa (p10). Similarly, granzyme B can cleave proCaspase 9 into a large subunit having an approximate molecular weight of 35 kDa (p35) and a small subunit having an approximate molecular weight of 12 kDa (p12). Moreover, other components of the apoptotic pathway can process Caspase 9 into a larger and a smaller cleavage product. Accordingly, the terms "large subunit" and "small subunit" will readily be understood to refer to any larger proteolytic cleavage product such as p37 or p35, and any smaller cleavage product such as p10 or p12, respectively.

Like other ASCPs, the active Caspase 9 complex can act as a protease and requires an Asp residue in the P1 position of the substrate binding site with a small, preferably hydrophobic, residue in the P1' position.

Apoptosis plays a significant role in numerous pathological conditions in that programmed cell death is either inhibited, resulting in increased cell survival, or enhanced, which results in the loss of cell viability. Examples of pathological conditions resulting from increased cell survival include cancers such as lymphomas, carcinomas and hormone-dependent tumors. Such hormone-dependent tumors include, for example, breast, prostate and ovarian cancer. Increased cell survival or apoptosis inhibition can also result in autoimmune diseases such as systemic lupus erythematosus and immune-mediated glomerulonephritis, as well as viral infections such as herpesvirus, poxvirus and adenovirus. The first gene identified as being involved in a cell death pathway, the bcl-2 gene, was identified in cancer cells and was shown to function by decreasing the likelihood that cells expressing the gene would undergo apoptosis.

In contrast, apoptotic diseases where enhanced programmed cell death is a prevalent cause generally includes, for example, degenerative disorders such as Alzheimer's disease, Parkinson's disease, Huntington's disease, amyotrophic lateral sclerosis, retinitis pigmentosa, cerebellar degeneration, and the encephalopathy associated with acquired immunodeficiency disease (AIDS). Since nerve cells generally do not divide in adults and, therefore, new cells are not available to replace the dying cells, the nerve cell death occurring in such diseases results in the progressively deteriorating condition of patients suffering from the disease. Other diseases associated with increased apoptosis include, for example, myelodysplastic syndromes such as aplastic anemia and ischemic injury, including myocardial infarction, stroke and reperfusion injury.

Caspase 9 inhibitors include those that inhibit protease activity as well as compounds that inhibit Caspase 9 binding to other polypeptides. Such compounds are useful as pharmaceuticals for treating or preventing diseases characterized by apoptotic cell death. When used in the present invention Caspase 9 polypeptides can be used to screen for compounds that activate or act as agonists of Caspase 9, such as by inducing cleavage of the proenzyme into its active subunits. Such compounds are similarly useful as pharmaceuticals for treating or preventing diseases characterized by the loss of apoptotic cell death.

SUMMARY OF THE INVENTION

This application relates to methods for identifying compounds that modulate Caspase 9 activity.

BRIEF DESCRIPTION OF THE DRAWINGS

FIGS. 4A through 4C show the selectivity of the Hofmeister salts for members of the caspase family. FIG. 4A shows Caspase 9 activity in varying amounts of ammonium sulfate. FIG. 4B shows Caspase 3 activity in varying amounts of ammonium sulfate.

FIG. 4C shows Caspase 9 activity in varying amounts of sodium phosphate.

DETAILED DESCRIPTION OF THE INVENTION

Figure 1A:
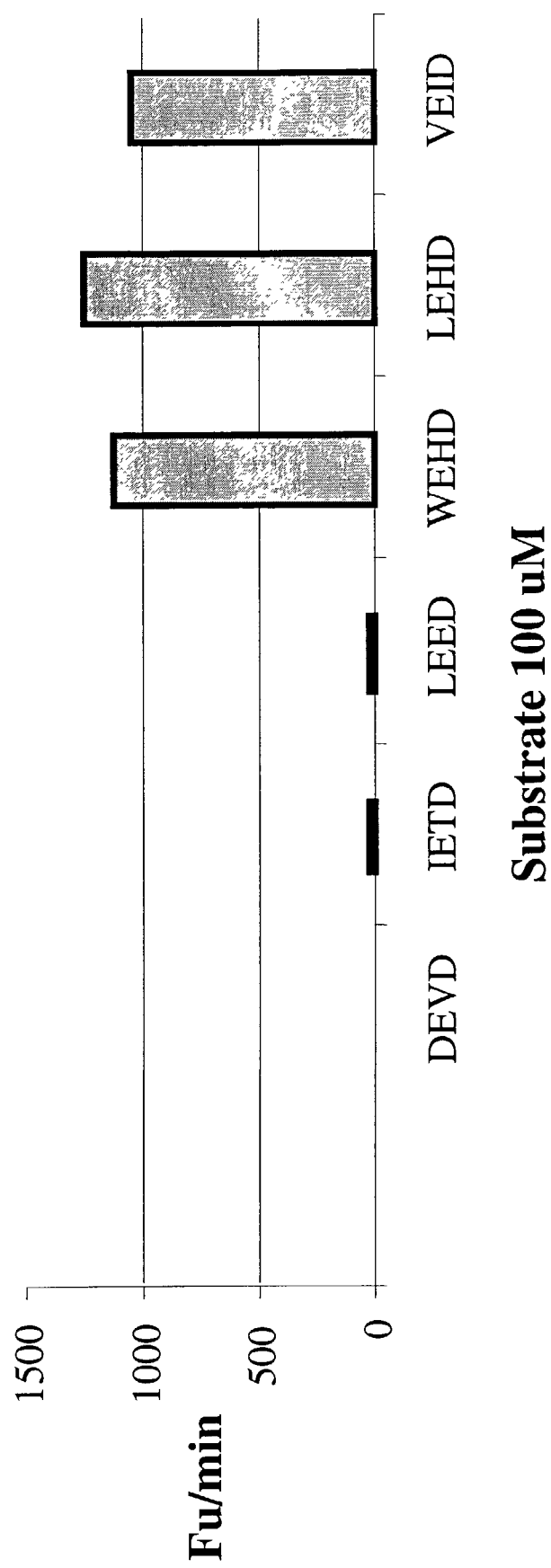
FIG. 1A shows the specificity of Caspase 1 in the substrates DEVD (SEQ ID NO: 1), IETD (SEQ ID NO: 2), LEED (SEQ ID NO: 3), WEHD (SEQ ID NO: 4), LEHD (SEQ ID NO: 5), and VEID (SEQ ID NO: 6) at pH 7.2.
Figure 1B:
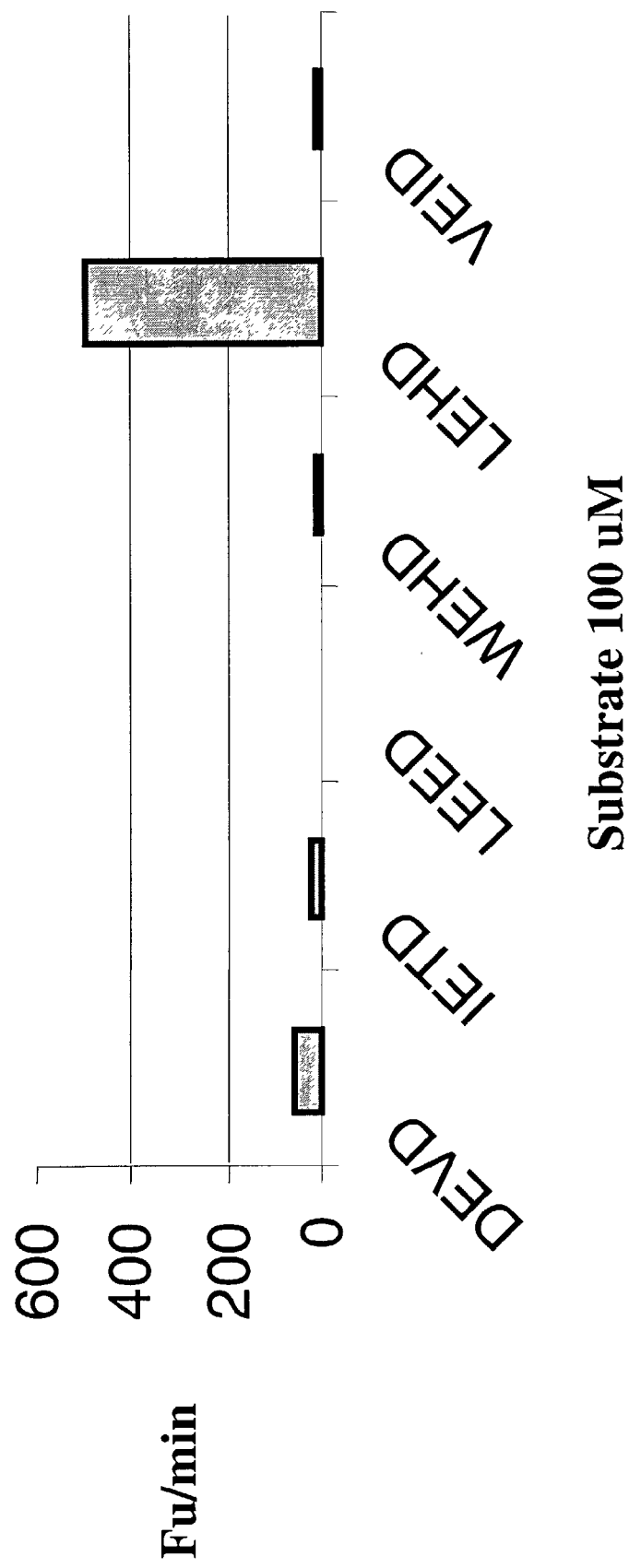
FIG. 1B shows the substrate specificity of Caspase 2 at pH 7.2.
Figure 1C:
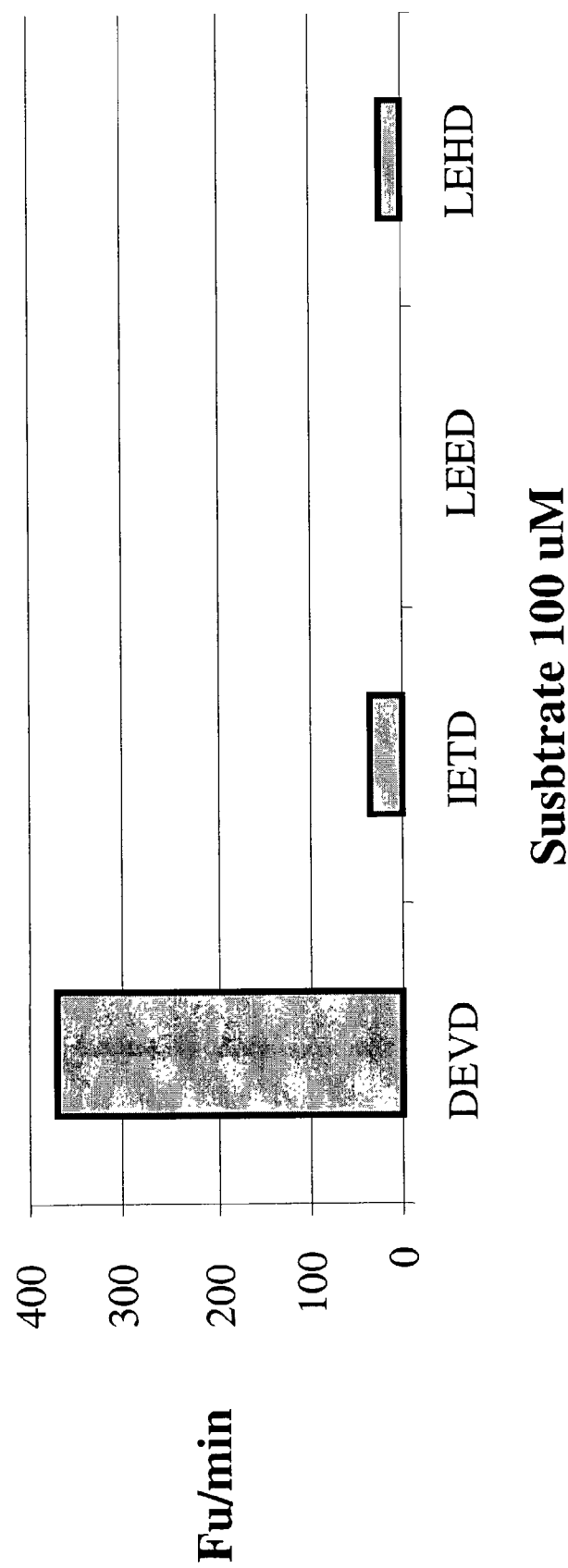
FIG. 1C shows the substrate specificity of Caspase 3 at pH 7.2.
Figure 1D:
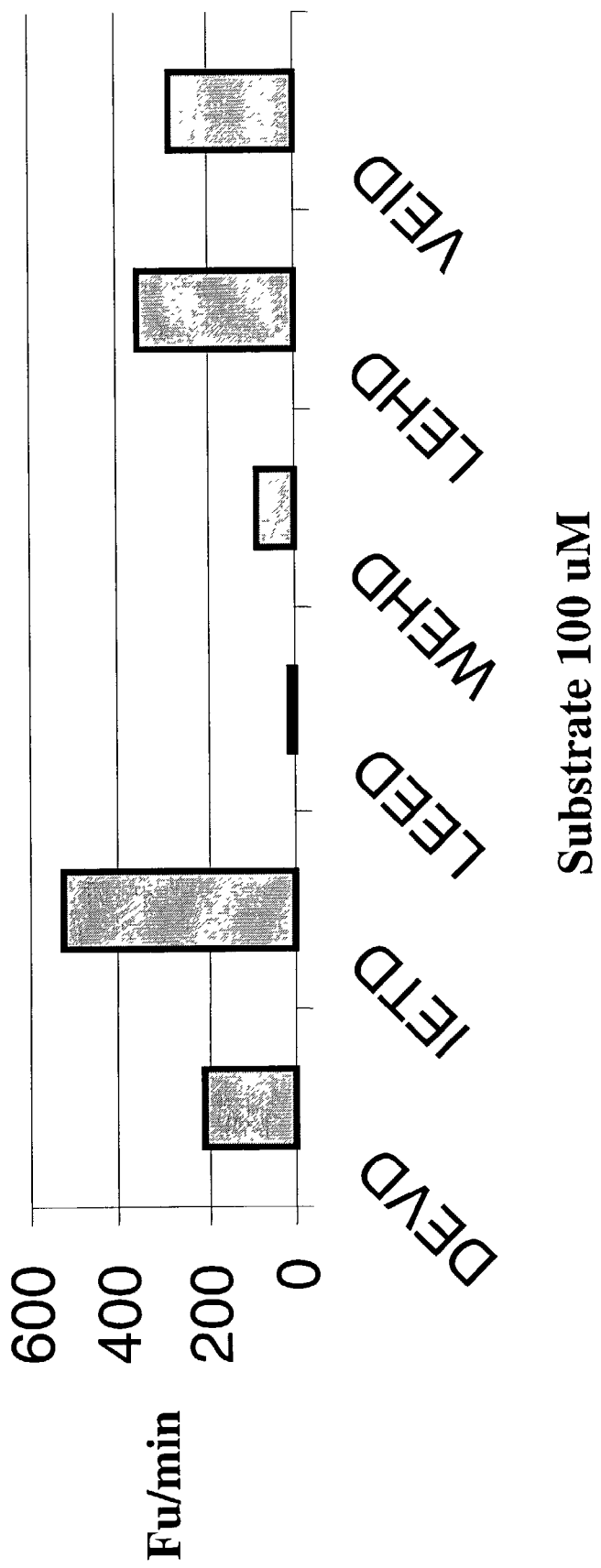
FIG. 1D shows the substrate specificity of Caspase 6 at pH 7.2.
Figure 1E:
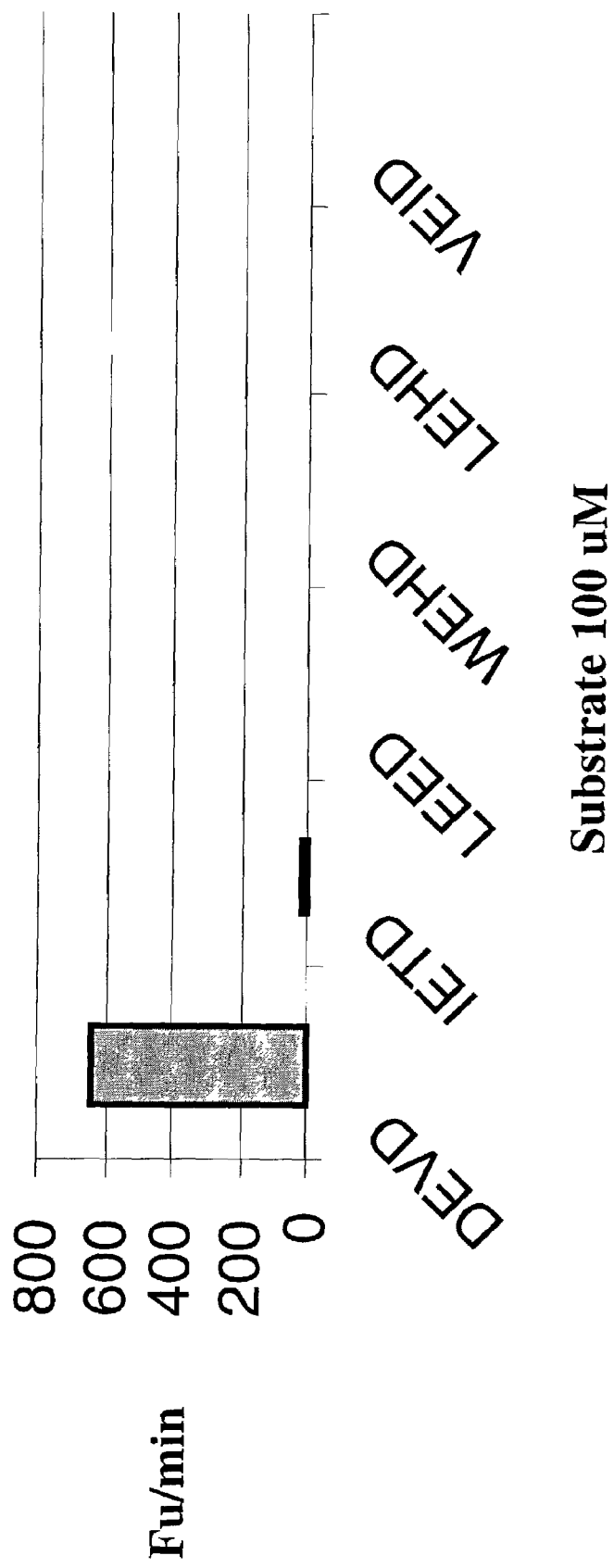
FIG. 1E shows the substrate specificity of Caspase 7 at pH 7.2.
Figure 1F:
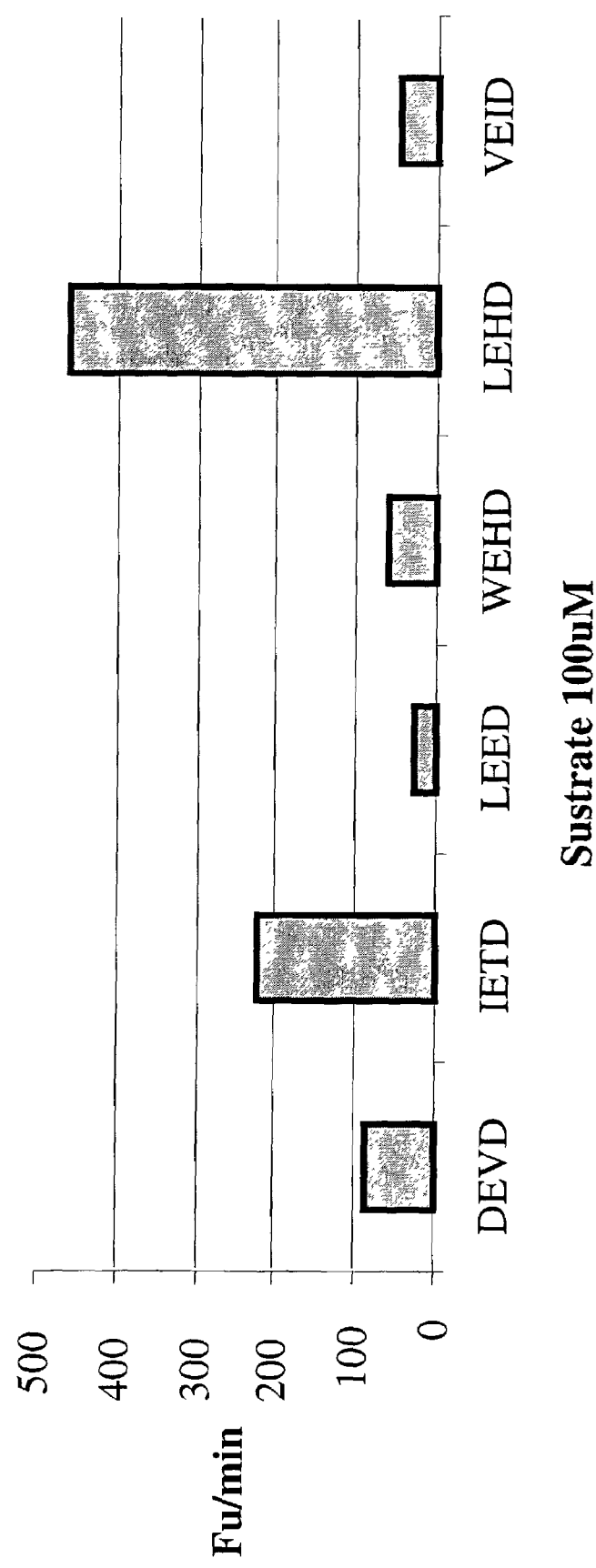
FIG. 1F shows the substrate specificity of Caspase 8 at pH 7.2.
Figure 1G:
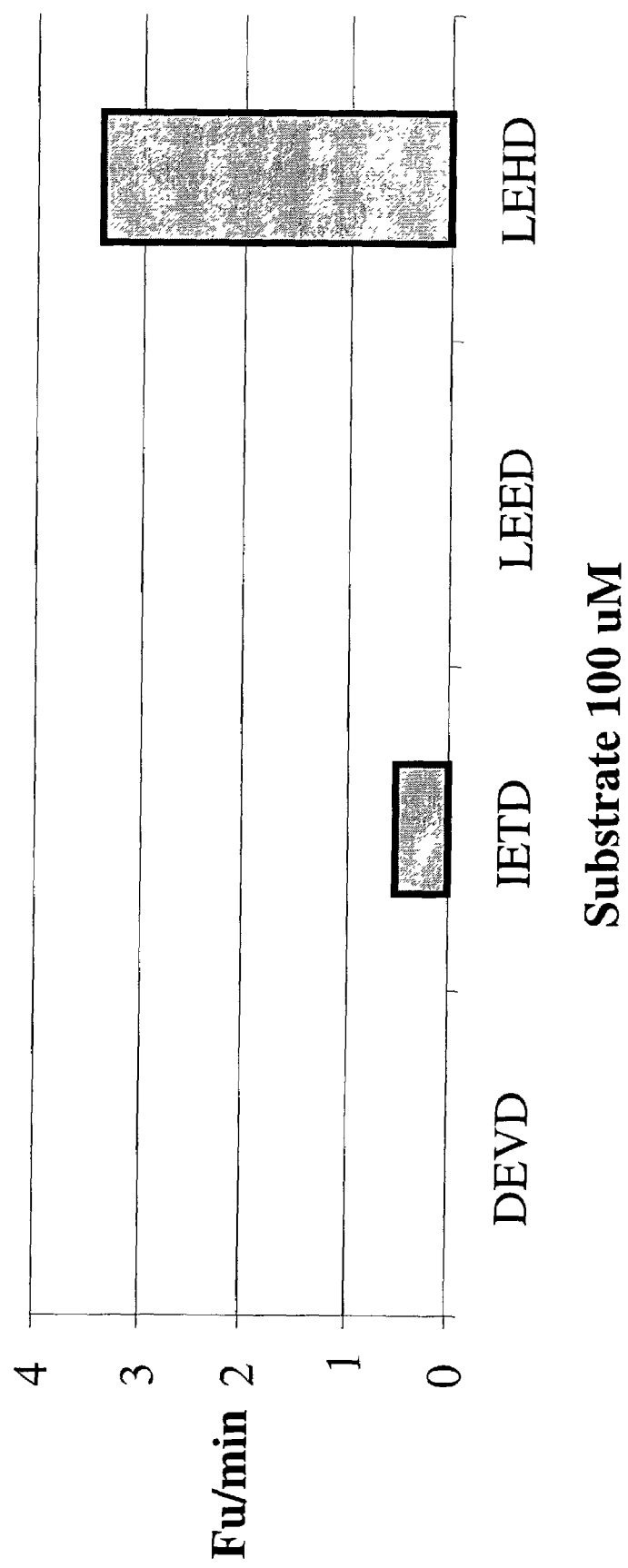
FIG. 1G shows the substrate specificity of Caspase 9 at pH 7.2.
Figure 1H:
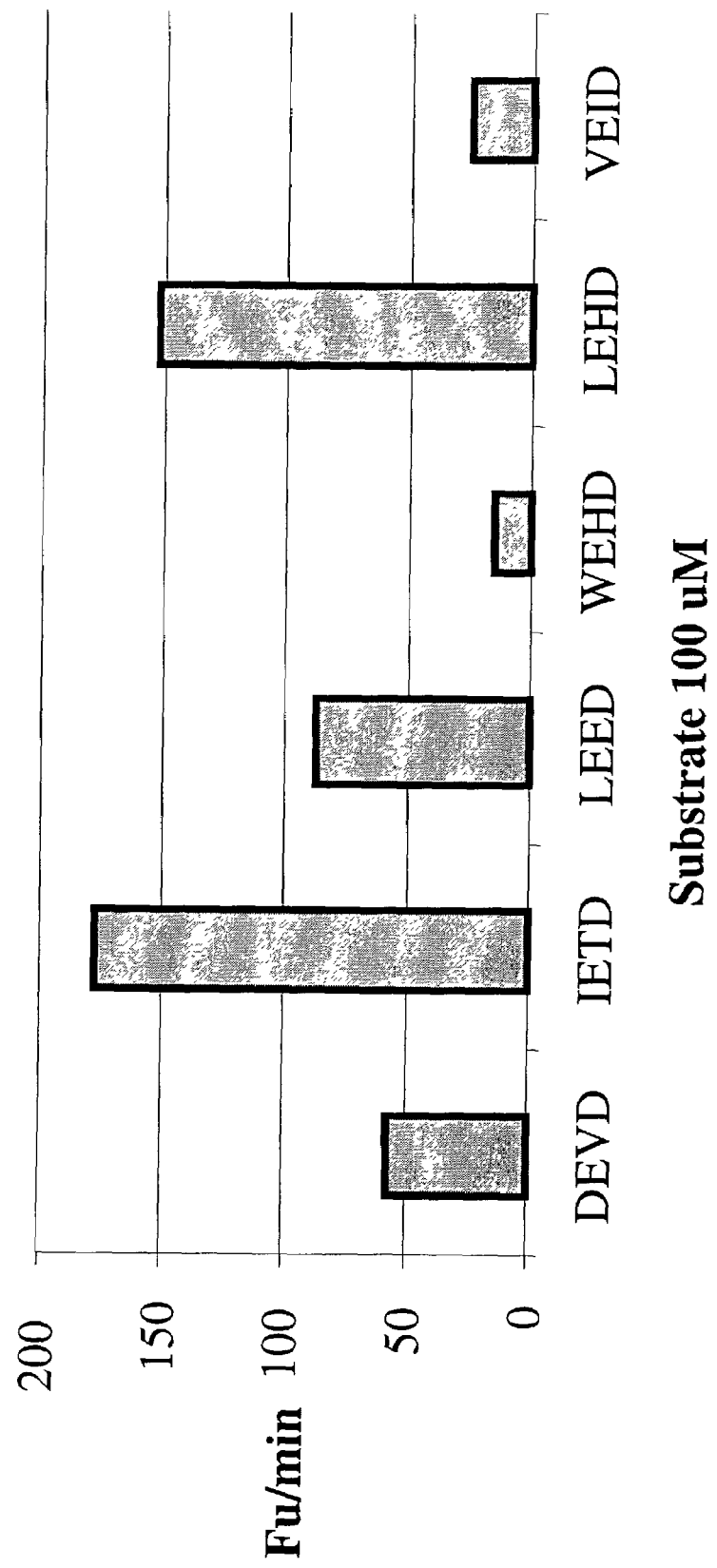
FIG. 1H shows the substrate specificity of Caspase 10 at pH 7.2.

Caspase 9 is the proteolytically active member of the multi-component assembly termed the apoptosome (Renatus, et al., (2001) Dimer formation drives the activation of the death protease Caspase 9, *PNAS* 98, 14250–14255). This complex controls the tissue architecture of the developing nervous system and the deletion of cells injured beyond recovery by environmental stress or ligand-receptor activation. Like other members of the caspase family, Caspase 9 exists in a latent form in of the cell, but unlike the others, simple proteolytic processing is insufficient for activation. Association with an activated form of APAF-1 in a 1-mega dalton complex is required for full catalytic conversion. The difficulties inherent in purifying each member of the complex and assembling them in vitro has greatly hindered efforts in gaining a structural understanding of Caspase 9 activation or using the protease in screens designed for discovering specific modulators. By providing a simple and convenient method for enhancing the activity of Caspase 9 in vitro this invention enables screening, including high throughput screening.

The Hofmeister series, below, originates from the ranking of various ions toward their ability to precipitate a mixture of hen egg white proteins.

| | |
|---|---|
| Anions: | $SCN^- > NO_3^- > Cl^- >$ citrate > acetate$^-$ > phosphate > $SO_4^{2-}$ |
| Cations: | $Ca^{2+} > Mg^{2+} > Na^+ = K^+ >$ $NH_4^+ > N(CH_3)_4^+$ |

Hofmeister series salts have been shown to have a much more general utility including showing the graduated effects on the structuring or denaturation of biological macromolecules. More recently the Hofmeister series are usually given in terms of the ability of the ions to stabilize the structure of proteins. A similar effect has been found with the salt-induced activation of lyophilised enzymes (Ru, et al. On the salt-induced activation of lyophilized enzymes in organic solvents: Effect of salt kosmotropicity on enzyme activity, J. Am. Chem. Soc. 122 (2000) 1565–1571). They show opposite correlation for anions and cations with their degree of strong hydration.

The relative positions (mostly corresponding to the degree of strong hydration) in the series should be thought of as indicative only, as there will be variation with protein, pH and temperature, with acetate ions showing pronounced cation-specific effects. Ions destroy the natural hydrogen bonded network of water, having effects similar to increased temperature or pressure; e.g. reduced viscosity. This effect of ions has been successfully approximated by the equivalent osmotic pressure. Ions that have the greatest such effect (exhibiting weaker interactions with water than water itself) are known as structure-breakers or chaotropes, whereas ions having the opposite effect are known as structure-makers or kosmotropes (exhibiting strong interactions with water molecules).

When Caspase 9 samples are prepared in ammonium sulfate rapid conversion of the substrate proteins to small peptides is observed, demonstrating dramatically increased proteolysis in this solution. Without limiting the generality of the mechanism, and without limiting the compositions and methods of the present application, the inventors postulate that the increased polarity of the aqueous solution by the dissolution of ammonium sulfate is responsible for a structural change in Caspase 9 by oligomerization or a conformational change with concomitant activation. A number of viral proteases are known to be activated by the water structuring anions (Kosmotropic agents) of the Hofmeister series (Cacace, M., Landau, E. and Ramsden, J. (1997), The Hofmeister series: salt and solvent effects on interfacial phenomena, *Quart. Rev. of Biophysics* 30, 241–277). For example, Herpes simplex virus 1 protease, responsible for maturation of the viral capsid, shows a 860-fold increase in activity in 1 M Na citrate (Hall, D. and Darke, P. (1995). Activation of the Herpes Simplex virus type 1 protease. JBC 270, 22697–22700). Treatment with this salt is thought to mimic the native microenvironment of the active protease, possibly in the nucleus with its attendant high concentration of polyanions.

Mimicking the activation of Caspase 9 in the apoptosome by modulating the solvent conditions for the protease leads to a simple in vitro screening procedure for discovering inhibitors of this enzyme.

The activation of Caspase 9 by kosmotropic agents is surprising not only in the extent of the activation but also in the fact that Caspase 9 is activated at all. Prior to the present invention there was no reason to believe that kosmotropic salts would activate Caspase 9. This fact is demonstrated by the failure of kosmotropic salts to activate other caspases such as Caspase 3 as described in Example 4.

Caspase 9 inhibitors can be used to treat or reduce the severity of diseases characterized by increased programmed cell death. Using assays as described herein for Caspase 9 activity, various compounds can be screened to discover compounds that inhibit or enhance the expression of Caspase 9 protease activity. Such screening methods are known to those skilled in the art. Such inhibitory molecules can be those contained in synthetic or naturally occurring compound libraries.

Caspase 9 inhibitors include, for example, small molecules and organic compounds that bind and inactivate Caspase 9 protease activity by a competitive or noncompetitive-type mechanism, inhibitors of the conversion of inactive proCaspase 9 into active Caspase 9 protease or other molecules that indirectly inhibit the Caspase 9 pathway. Such Caspase 9 inhibitors can include, for example, suicide inhibitors, anti-Caspase 9 antibodies and proteins, small peptide protease inhibitors, or small non-peptide organic molecule inhibitors. Specific examples of such inhibitors include substrate analogs such as tetrapeptide DEVD-CHO (SEQ ID NO: 1) (Asp-Glu-Val-Asp-aldehyde), fluorescently labeled tetrapeptide: such as DEVD-AMC (SEQ ID NO: 1) (Asp-Glu-Val-Asp-aminomethylcoumarin), YVAD-AMC (SEQ ID NO: 7) (Tyr-Val-Ala-Asp-aminomethylcoumarin), ZEVD-AMC (carbobenzoxy-Glu-Val-Asp-aminomethylcoumarin) and the cowpox virus protein Crm A. Another specific example includes phage display peptide libraries where greater than $10^8$ peptide sequences can be screened in a single round of panning (U.S. Pat. No. 6,121, 416). Caspase 9 inhibitors can be formulated in a medium that allows introduction into the desired cell type or can be attached to targeting ligands for introduction by cell-mediated endocytosis and other receptor-mediated events.

Caspase 9 substrate antagonists can be used to treat or reduce the severity of diseases mediated by increased programmed cell death. Such substrate antagonists can bind to and inhibit cleavage by Caspase 9. Inhibition of substrate cleavage prevents commitment progression of programmed cell death. Substrate antagonists include, for example, ligands and small molecular compounds.

Caspase 9 inhibitors can also be identified using Caspase 9-encoding nucleic acids and the Caspase 9 polypeptide of the invention in, for example, binding assays such as ELISA or RIA, or enzymatic assays using tetrapeptide substrates, such as courmarin labeled DEVD-AMC (SEQ ID NO: 1) and YVAD-AMC (SEQ ID NO: 7). DEVD-AMC (SEQ ID NO: 1) and YVAD-AMC (SEQ ID NO: 7) represent cleavage sites for the poly(ADP-ribose) polymerase (PARP) and IL-1β: P1–P4 substrate tetrapeptides, respectively (Nicholson et al., Nature 376:37–43 (1995)).

The Caspase 9 polypeptide to be used in such assays can be obtained by, for example, in vitro translation, recombinant expression or biochemical procedures. Such and other methods are known within the art. For example, recombinant Caspase 9 can be expressed by cloning Caspase 9 cDNA into a bacterial expression vector such as pET21b (Novagen Inc., Madison, Wis.). The Caspase 9 can then be expressed and purified using routine molecular biology methods known to those skilled in the art. A purified recombinant Caspase 9 protein can be used to measure hydrolysis rates for various substrates, such as DEVD-AMC (SEQ ID NO: 1) and YVAD-AMC (SEQ ID NO: 7) in a continuous fluorometric assay.

Numerous methods are known in the art for measuring caspase activity including using fluorogenic substrates of the caspase, enzyme activity assays, immunoblotting, and affinity labeling as described in *Current Protocols in Cell Biology*, Chapter 18 which is hereby incorporated by reference in its entirety. Prior to the present invention these methods were not useful for Caspase 9 because of its low activity level in vitro.

Once Caspase 9 is activated using the techniques disclosed herein its activity can be quantified using a fluorescent assay. In one embodiment 7-amino-trifluoromethyl coumarin (AFC) is used. AFC fluoresces when cleaved from a peptide, such as Ac-LEHD-AFC (SEQ ID NO: 5) because it is no longer quenched by the acetyl (Ac) blocking group. AFC excitation occurs at 400 nm and its fluorescence is 505 nm. When the peptide is intact this fluorescence is quenched by the presence of the blocking Ac (acetyl) group on the N-terminal of the peptide because the both groups are so close in distance. Caspase 9 cleaves after the D (asp) and releases the AFC group which is then not quenched by the blocking group.

High-throughput screening of caspases other than Caspase 9 is known in the art. For example, Caspase 8 was screened by Smith et al. (Expression, preparation, and high-throughput screening of Caspase-8: discovery of redox-based and steroid diacid inhibition, *Arch Biochem Biophys* 2002 Mar. 15; 399(2):195–205, incorporated herein by reference in its entirety) as follows: an *Escherichia coli* expression construct for Caspase-8 was constructed in which a His-tag sequence is inserted 5' of codon 217 of Caspase-8. The strain produced a significant amount of soluble His-tagged 31-kDa inactive single-chain enzyme precursor. This 31-kDa protein was purified to 98% purity. Hydroxyapatite column chromatography resolved the enzyme into two species, one with the appropriate 31,090 relative mass and the other with 178 additional mass units (i.e., 31, 268). The latter proved to result from *E. coli*-based modification of the His-tag with one equivalent of glucono-1,5-lactone. The purified proteins were activated by autoproteolysis to the appropriate 19-plus 11-kDa enzyme by the addition of dithiothreitol in appropriate buffer conditions. This yielded an enzyme with specific activity of 4–5 units/mg (U/mg) against 200 microM Ac-IETD-pNA (SEQ ID NO: 2) at 25 degrees Celcius (C). The fully active protein was used in a high-throughput screen for inhibitors of Caspase-8. A preliminary robustness screen demonstrated that Caspase-8 is susceptible to reactive oxygen-based inactivation in the presence of dithiothreitol (DTT) reducing agent but not in the presence of cysteine. Investigation into the mechanism of this inactivation showed that quinone-like compounds were reduced by DTT establishing a reactive oxygen generating redox cycle the products of which (likely H(2)O(2)) inactivated the enzyme. Caspase-8 inhibitors and steroid-derived diacids with affinity in the low micromolar range were uncovered in the screen. Structure-activity investigation of the inhibitors showed that both the steroid template and the acid moieties were required for activity. One skilled in the art will recognize how the present invention can be used to modify such existing screening methods to accommodate Caspase 9 which previously could not be screened in a meaningful way.

It is understood that modifications that do not substantially affect the activity of the various embodiments of this invention are also included within the definition of the invention provided herein. Accordingly, the following examples are intended to illustrate but not limit the present invention.

EXAMPLE 1

Substrate Specificity of Commercially Available Caspases

A panel of commercially available caspases was tested against a series of substrates to assess the specificity of each protease. The preferred substrate of Caspase 9 was the tetrapeptide, Lysine-Glutamate-Histidine-Aspartate (herein after LEHD (SEQ ID NO: 5)). In addition, Caspase 9 in neutral buffered saline has an activity level which is orders of magnitude lower against its preferred substrate (LEHD (SEQ ID NO: 5)) than any of the other caspases versus their cognate tetrapeptide. These results demonstrate the difficulty in the art, prior to the present invention, encountered when attempts have been made to screen for Caspase 9 modulators.

The control buffer used to carry out specificity reactions is as follows: 20 mM PIPES pH 7.2, 1 mM EDTA, 0.1% CHAPS, 10% sucrose, 10 mM DTT. Various N-acetyl-tetrapeptide-7-amino-trifluoromethylcoumarin substrates at 100 uM were assayed with the different commercially available caspases. 2.5 mM stock substrate concentrations were prepared in DMSO and subsequently diluted to 200 uM with control buffer.

300 U stock solutions of the enzymes in interest were prepared in the control buffer listed above. The assay was carried out as follows: 96 well black Dynex microfluorometer 1 plate was used. Total Assay volume was 100 ul. 7-amino-trifluoromethyl coumarin (AFC) was excited at 400 nm, and fluorescence emission was monitored at 505 nm kinetically for the duration of 1 hour (h) wherein AFC was cleaved from the peptide.

50 ul of 200 uM stock substrate was added first (final assay concentration 100 uM). 40 ul of the control buffer was then added. The assay was initiated with the addition of 10 ul of the appropriate 300 U caspase stock (30 U in final assay). A linear rate (relative fluorescence U/s) was calculated from the entire duration of the experiment and graphed for each enzyme verses the various substrates tested.

EXAMPLE 2

A Comparison of Cleavage Rates by Various Caspases

Figure 2:
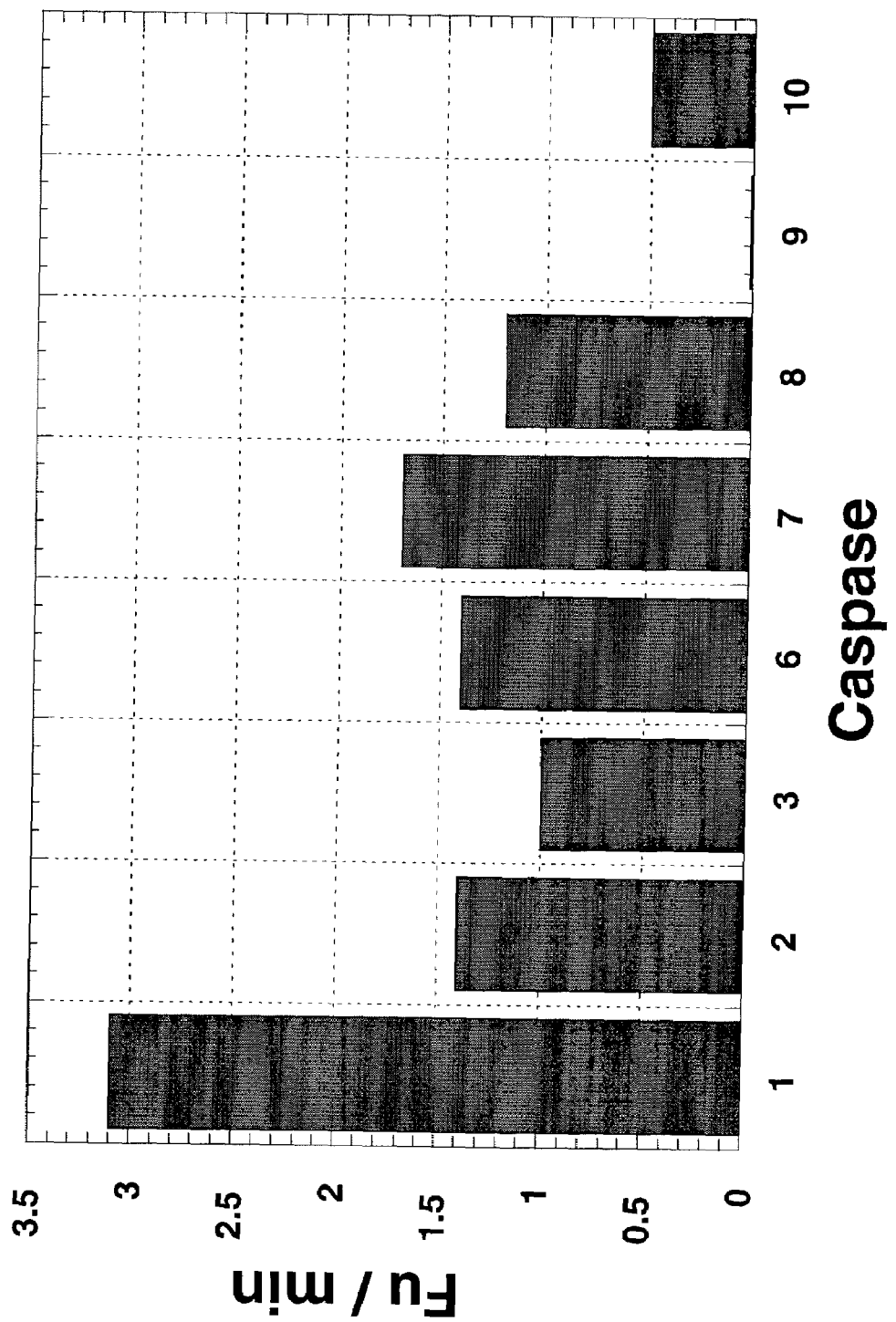
FIG. 2 shows the rates of AFC release relative to the caspase type.

The relative rates of cleavage of various caspases for their optimal substrates as compared to Caspase 3 and its preferred tetrapeptide, DEVD (SEQ ID NO: 1), was determined. The assays were carried out in the procedure listed above in the description for Example 1. The results are presented in FIG. 2. FIG. 2 shows the relative activity between enzymes using 30 U and their optimal substrates. As shown previously, Caspase 9 has an activity far lower than any of the other caspases in neutral buffered saline. Table 1 shows the concentration of caspases used to generate the data in FIG. 2 as well as the optimal substrate for each enzyme.

TABLE 1

| Caspase | Caspase (uM in assay) | Optimum substrate at pH 7.2 |
| --- | --- | --- |
| 1 | 0.024 | Ac-WEHD-Afc (SEQ ID NO:4), Ac-LEHD-Afc (SEQ ID NO:5), Ac-VEID-Afc (SEQ ID NO:6) |
| 2 | 0.0017 | Ac-LEHD-Afc (SEQ ID NO:5) |

TABLE 1-continued

| Caspase | Caspase (uM in assay) | Optimum substrate at pH 7.2 |
| --- | --- | --- |
| 3 | 0.0012 | Ac-DEVD-Afc (SEQ ID NO:1) |
| *6 | 0.313 | Ac-IETD-Afc (SEQ ID NO:2) |
| *7 | 0.275 | Ac-DEVD-Afc (SEQ ID NO:1) |
| 8 | 0.0019 | Ac-LEHD-Afc (SEQ ID NO:5) |
| *9 | 0.72 | Ac-LEHD-Afc (SEQ ID NO:5) |
| 10 | 0.068 | Ac-IETD-Afc (SEQ ID NO:2), Ac-LEHD-Afc (SEQ ID NO:5) |

EXAMPLE 3

Relative Rates of LEHD (SEQ ID NO: 5) Cleavage by Caspase 9 in Buffers Containing the Na Salts of the Hofmeister Series All salts were dissolved in the control buffer to a concentration of 0.8 M. The buffer was: 20 mM PIPES pH 7.2, 1 mM EDTA, 0.1% CHAPS, 10% sucrose, 10 mM DTT. The substrate was: 100 uM N-Ac-LEHD-Afc (SEQ ID NO: 5), 30 U Caspase 9/well (0.72 uM).

Figure 3:
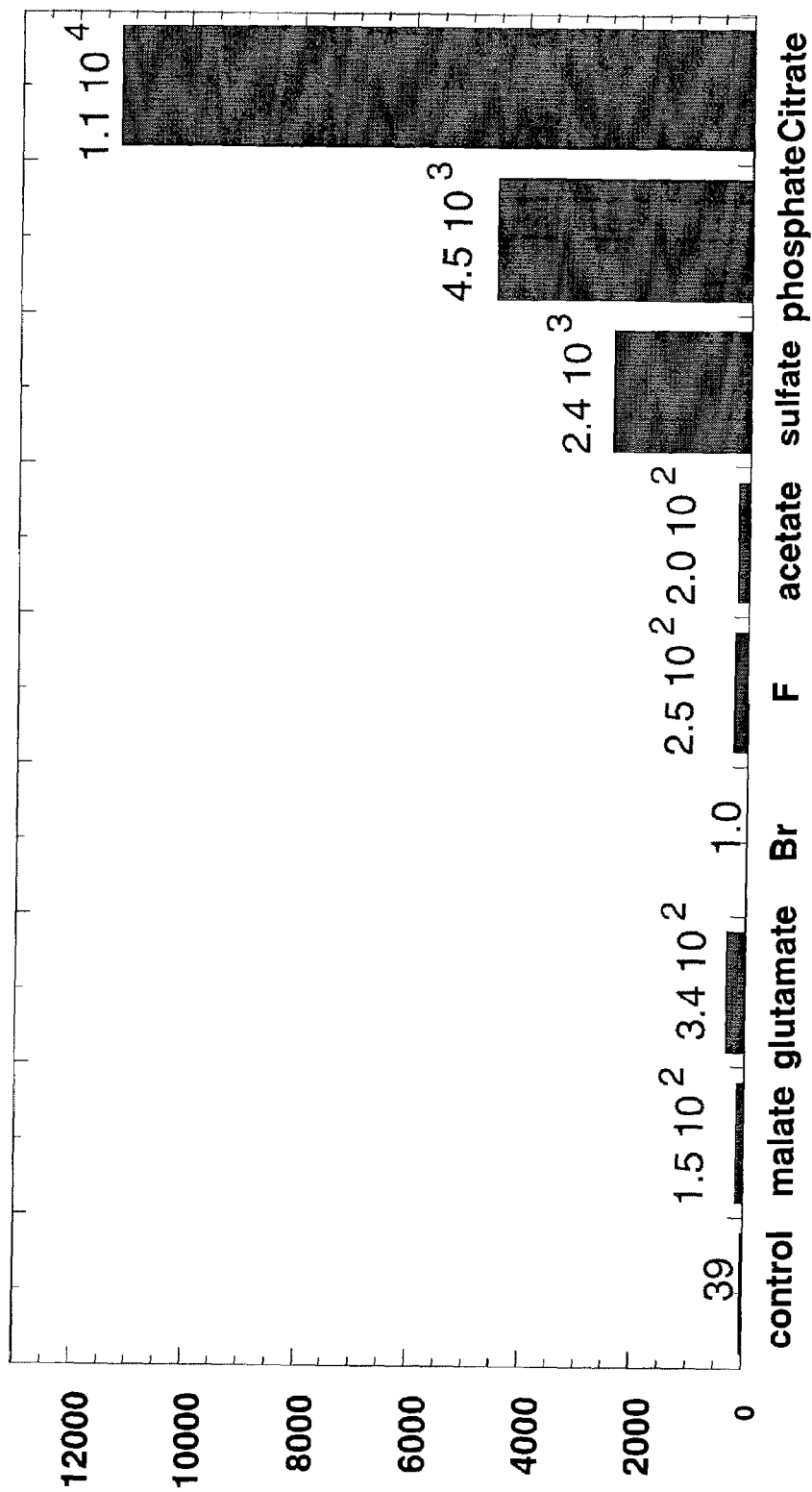
FIG. 3 shows the relative rates of LEHD (SEQ ID NO: 5) cleavage by Caspase 9 in buffers containing the Na salts of the Hofmeister series.

The proteolytic activity correlates with the increasing water-structuring potential of the Hofmeister anions with citrate>phosphate>sulfate>acetate. The activity of Caspase 9 in 0.8 M citrate is 10,000-fold higher than the relative activity in 0.8 M bromide, which is considered a structure destabilizing anion (see FIG. 3).

EXAMPLE 4

The Activity of Members of the Caspase Family by Hofmeister Salts

Figure 4A:
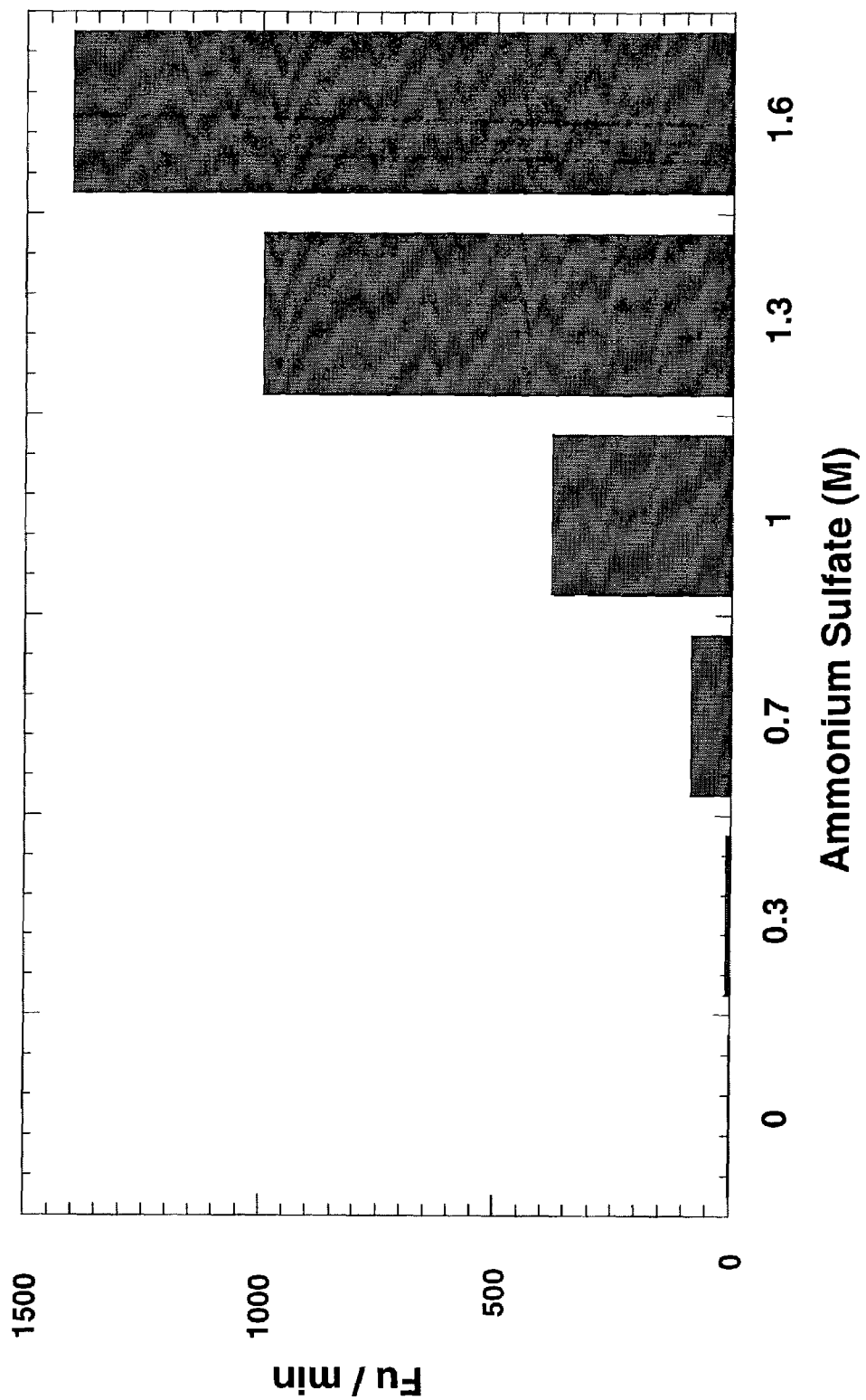
Figure 4C:
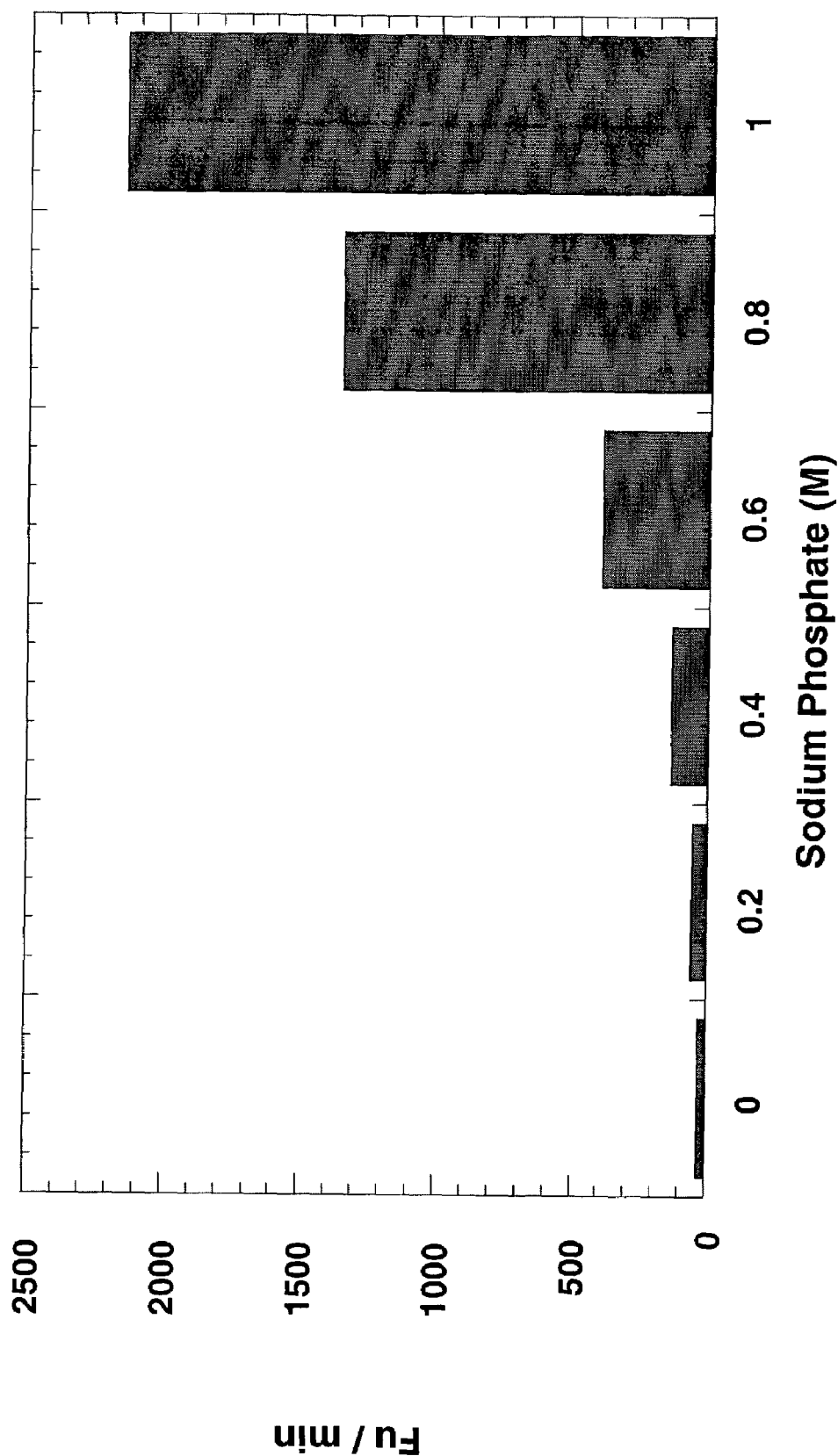
Figure 5A:
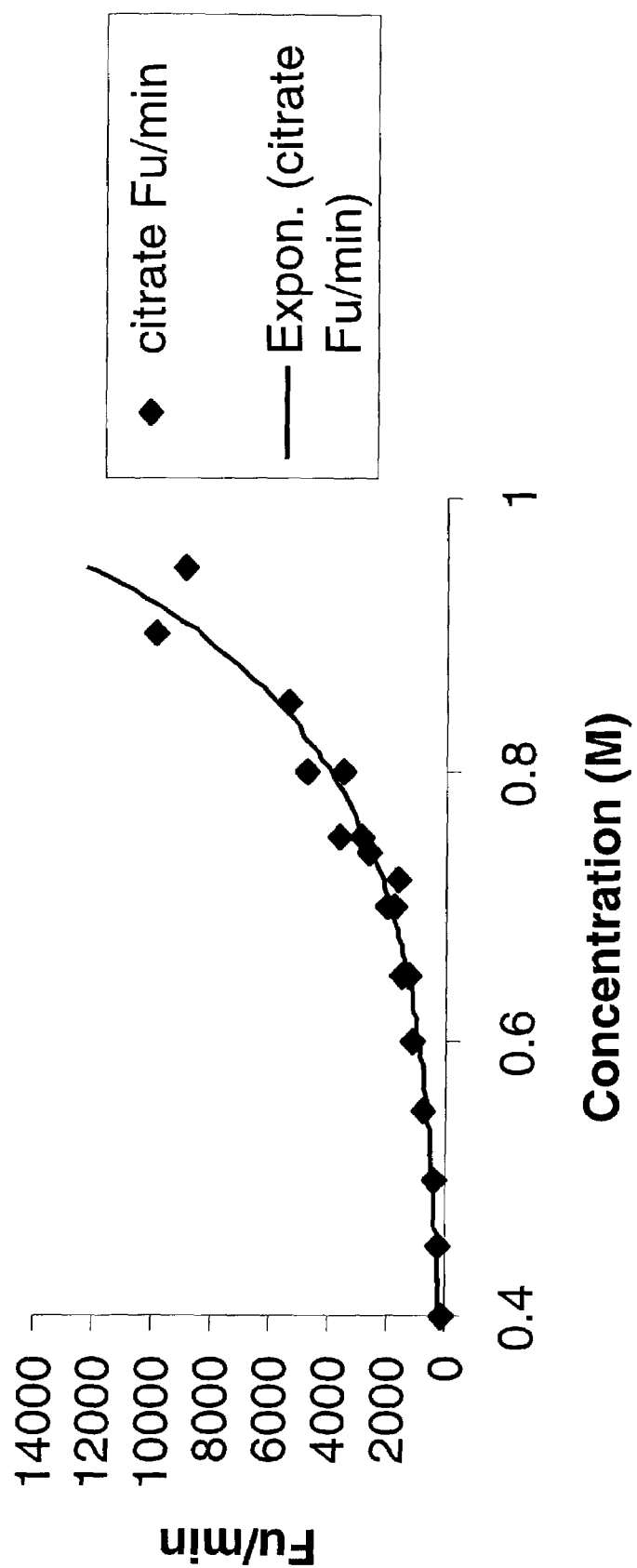
FIG. 5A shows Caspase 9 activity in 30 U enzyme, 100 uM Ac-LEHD-AFC (SEQ ID NO: 5) in varying Na citrate concentrations.
Figure 5B:
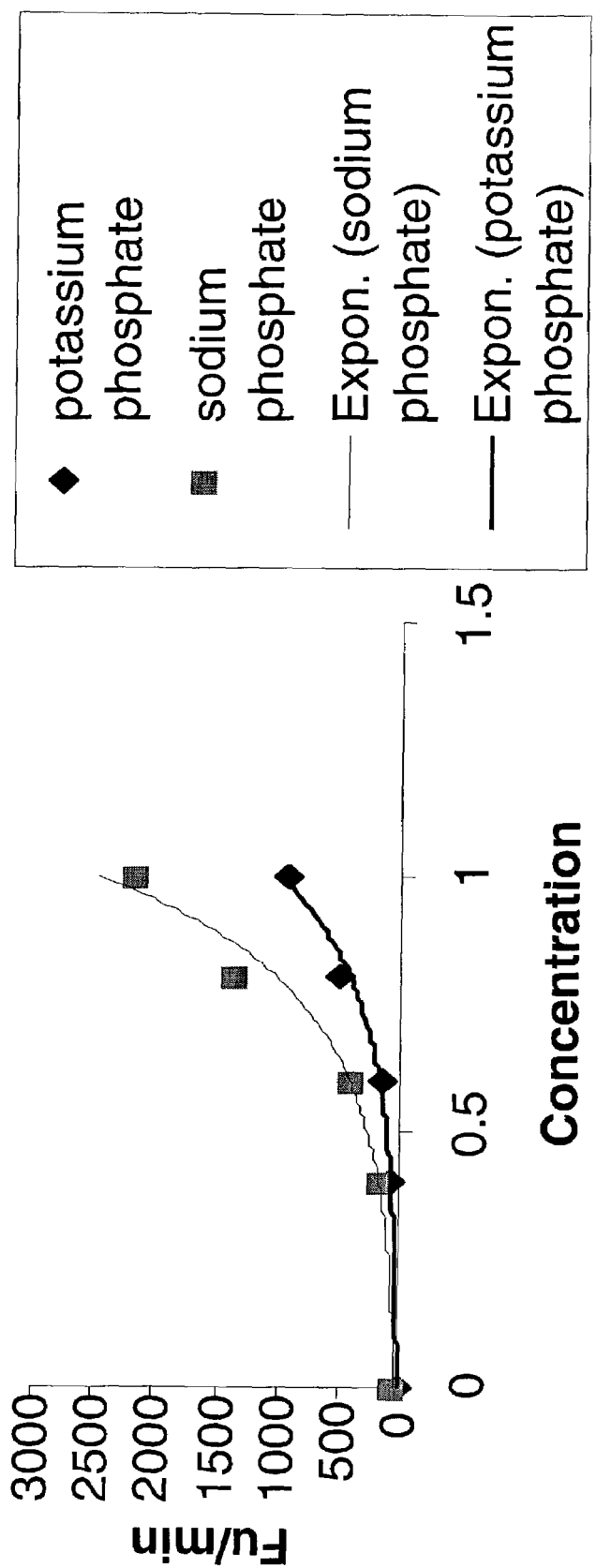
FIG. 5B shows Caspase 9 activity in 30 U enzyme, 100 uM Ac-LEHD-AFC (SEQ ID NO: 5) in varying Na and K phosphate solutions.
Figure 5C:
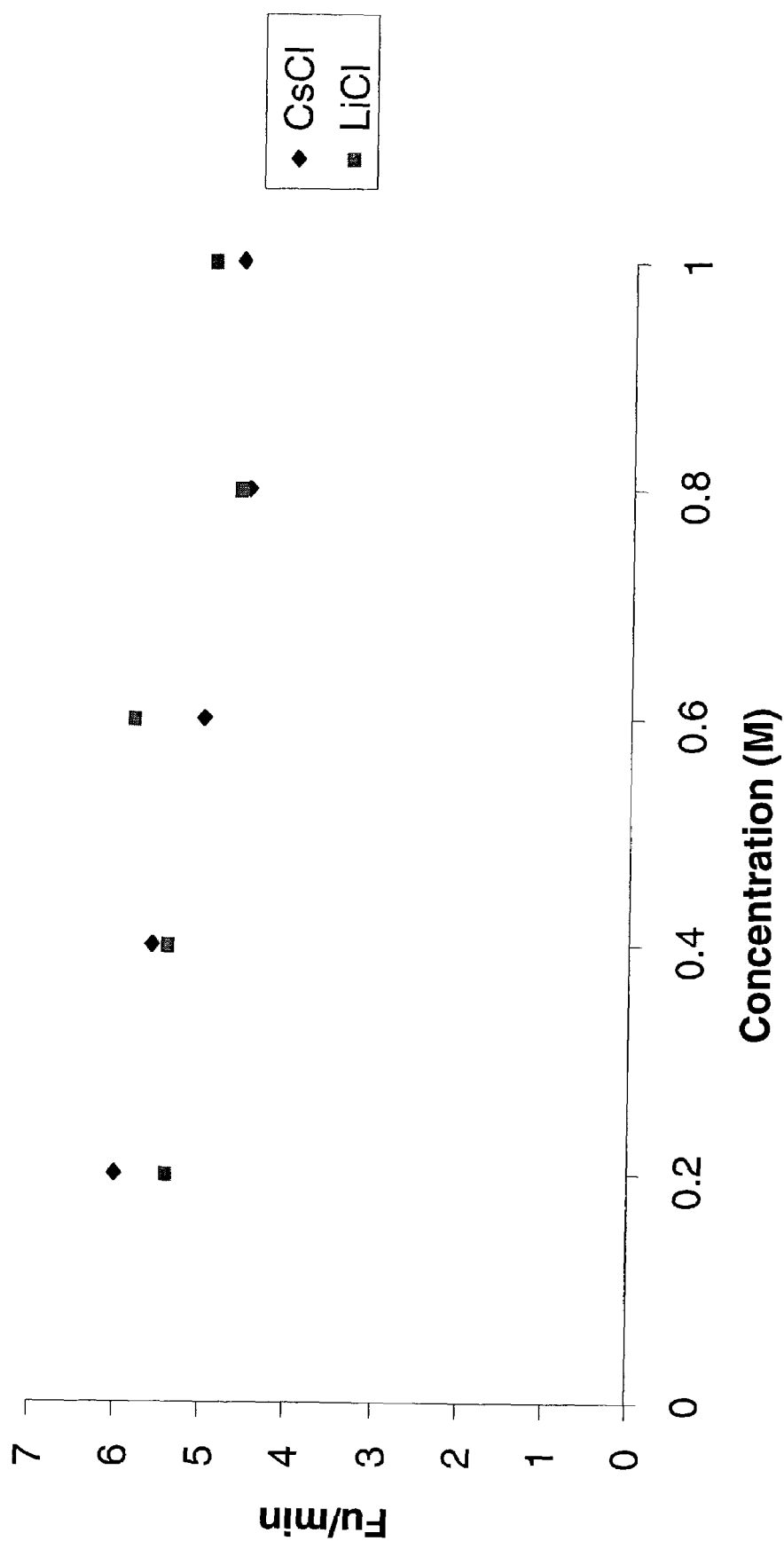
FIG. 5C shows Caspase 9 activity in varying concentrations of CsCl and LiCl.
Figure 5D:
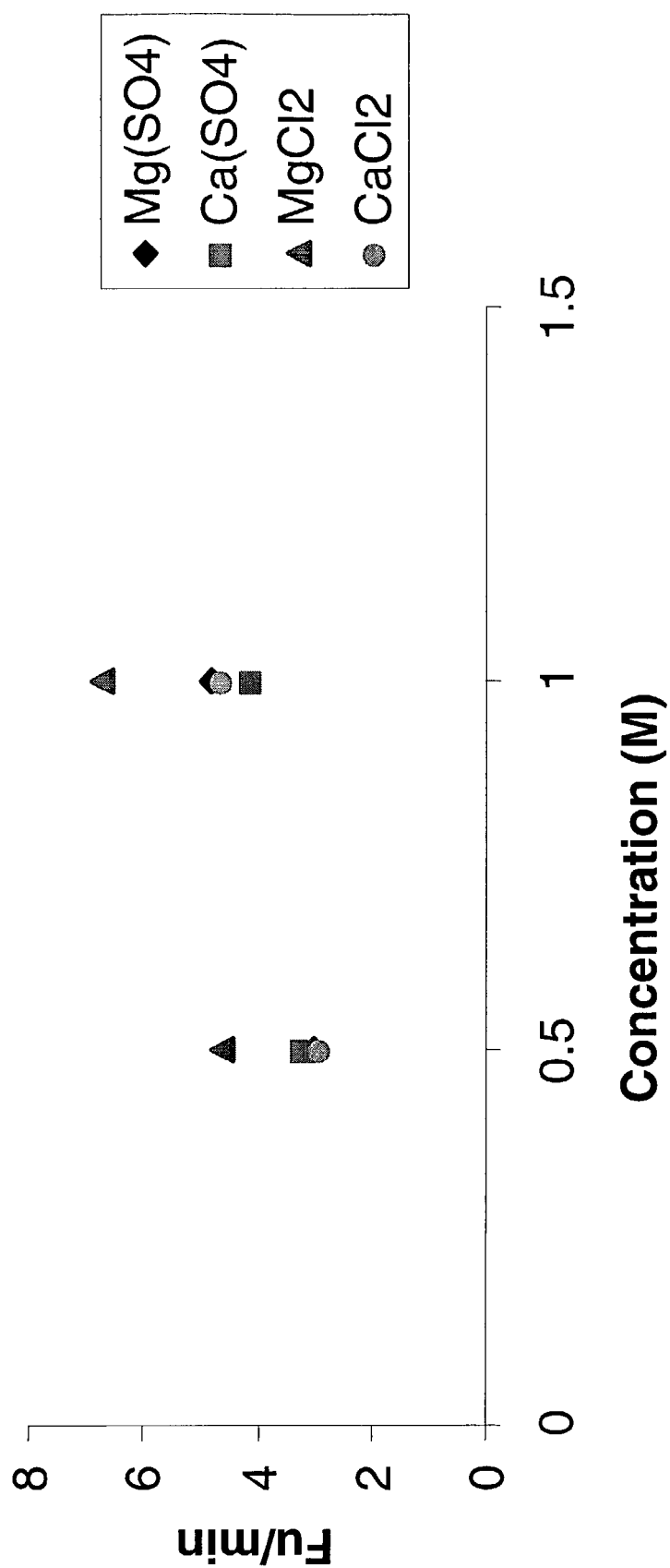
FIG. 5D shows Caspase 9 activity in varying concentrations of $Mg(SO_4)$, $Ca(SO_4)$, $MgCl_2$, and $CaCl_2$.

Caspases 1, 3, 7, and 9 were assayed using ammonium sulfate at various concentrations and Caspase 9 was further assayed with sodium phosphate at various concentrations. The salts had no effect on Caspases 1 and 7 and minimal effect on Caspase 3 as shown in FIG. 4. In contrast, Caspase 9 shows a 1400-fold activity increase in a range of sulfate concentrations from 0 to 1.6 M (FIG. 4A) and a 2200-fold increase in a range of phosphate concentrations from 0 to 1 M. Buffers used are as described in Example 1. The substrates in ammonium sulfate using Caspase 9 was 25 uM Ac-LEHD-Afc (SEQ ID NO: 5) and for Caspase 3 was 25 uM Ac-DEVD-Afc (SEQ ID NO: 1). In Na phosphate the substrate for Caspase 9 was 100 uM Ac-LEHD-Afc (SEQ ID NO: 5).

EXAMPLE 5

Caspase 9 Activity in Varying Hofmeister Salts

Caspase 9 activity was determined in various Hofmeister Salts including both anions and cations. The results show that the more weakly organizing cations of the Hofmeister series also increase the activity, however, the increase is not as strong as for the anions, as predicted by the theory behind the Hofmeister series, discussed above. The results are shown in FIG. 5. 30 U of enzyme was used (0.72 uM), the substrate was 100 uM Ac-LEHD-AFC (SEQ ID NO: 5) and the buffer was described in Example 1.

EXAMPLE 6

High Throughput Screening of Caspase 9 utilizing a Hofmeister Salt

The following general protocol for a high throughput screen is built around the observation, explained in Examples 3 and 4, that an acceptable enhancement of Caspase 9 activity can be achieved with 0.8 M Na citrate contained in the reaction buffer. The screen consists of mixing recombinant Caspase 9, its fluorogenic substrate, LEHD-AFC (SEQ ID NO: 5), and the test compounds in a buffer containing 0.8 M citrate in a 96-well format and following the enzyme kinetics with an automated spectrofluorometer. All manipulations can be automated using robots.

An example of a detailed protocol would be the following: all reagents would be ultimately diluted in the reaction buffer (20 mM PIPES, pH 7.2, 1 mM EDTA, 0.1% CHAPS, 10% sucrose, 0.8 M Na citrate, pH 7.2, 1 mM cysteine) to be referred to as buffer A. Stock substrate, LEHD-AFC (SEQ ID NO: 5) (Enzyme Systems Products), is made up to 2.5 mM in DMSO. Stock inhibitor peptide, LEHD-CHO (SEQ ID NO: 5) (Enzyme Systems Products), and test compounds are made up to 10 mM in DMSO. Stock Caspase 9 (PharMingen, San Diego, Calif.) is made up to 300 U/100 ul in buffer A. Reactions will take place in a 100 ul volume in individual wells of u-bottomed black 96-well plate. Reaction mix is formulated by the following: 1. Dilute stock substrate 1:50 in buffer A to a concentration of 50 uM, this is referred to as substrate mix, 2. Dilute stock compounds 1:40 in buffer A to 250 uM, this is referred to as compound mix. The reaction is primed by adding 50 ul of substrate mix and 40 ul of compound mix in individual wells and started by the addition of 10 ul of stock Caspase 9. The resultant concentrations of Caspase 9, substrate and compound is 10 U/100 ul, 25 uM and 100 uM respectively. Proteolytic activity is monitored kinetically as fluorescent U/second (U/s) over the period of 1 h at room temperature. Each reaction is in triplicate. Proper controls consist of wells containing the following: 1. Substrate alone (negative control); 2. Substrate and enzyme (positive control); 3. Substrate, enzyme and peptide inhibitor (inhibitor control). These controls are followed by substrate, enzyme and test compounds. Positive hits are scored as any compound reducing the activity of Caspase 9 by =>50%.

EXAMPLE 7

Screening for Inhibitors of Caspase 9 Allosteric Activation

Caspase 9 activation in the cell is dependent on an allosteric interaction with the apoptosome, a 1 megadalton association of proteins containing APAF 1, cytochrome C and Caspase 9. The introduction of purified Caspase 9 into buffers containing kosmotropic salts of the Hofmeister series mimics the allosteric activation state of Caspase 9 in the apoptosome. This enables screening for molecules that bind to the activation region of Caspase 9 and are distinct from molecules that bind to the catalytic site of the protease. This is accomplished by initially screening for compounds that inhibit the cleavage of a fluorescent tetrapeptide specific for Caspase 9 (LEHD (SEQ ID NO: 5)) in 0.8 M Na citrate (see Example 6). The resultant hits are either inhibitory due to binding in the catalytic cleft or due to binding the remote allosteric site and changing the conformation of the protease to its inactive form. The hits are then differentiated in a secondary screen by competitive displacement of the compounds by the cognate tetrapeptide, LEHD (SEQ ID NO: 5), which binds only in the catalytic site. Release of inhibition by competitive replacement of the inhibitory compound by tetrapeptide differentiates molecules interacting at the catalytic site from those acting at the allosteric site.

A detailed description of a simple protocol is as follows: all hits from the primary screen are collected and diluted to 250 uM (1:40), 25 uM (1:400) and 2.5 uM (1:4000) with buffer A (Example 6). 40 ul of each of these compound mixes is added to individual wells in a 96-well plate in triplicate and 10 ul of enzyme stock is then added and allowed to pre-incubate for 10 min at room temperature. After this period, the reaction is started by addition of 50 ul of substrate mix (Example 6). The resultant concentrations of each reactant are 30 U/100 ul Caspase 9, 25 uM substrate and 100 uM, 10 uM and 1 uM of primary screen hit compound. Enzyme kinetics are followed by a spectrafluorometer over the period of 1 h. Competitive displacement of inhibitory compound by substrate is detected by non-linear kinetics at one or more compound concentrations with a pronounced lag time before the final rate is obtained. Linear kinetics from time 0 or non-release from inhibition is an indication of either allosteric inhibition or a non-competetive type inhibition, respectively.

The structural basis of all inhibitor-enzyme relationships may be ultimately defined by X-ray chrystallography or solution NMR.

One skilled in the art will recognize that variations of this procedure can be easily formulated such as substituting dithiothreitol (DTT) or glutathione for cysteine. These variations are all essentially equivalent to the present protocol although they will of course vary in their usefulness according to the particular set of conditions used.

Typical reaction conditions for a high-throughput screen include: 50 ul substrate in 120% buffer+40 ul enzyme in 100% buffer+10 ul sample in 50 mM HEPES.

Buffer pH 7.2 for Enzymes

| | |
|---|---|
| 20 mM PIPES [pH to 7.2 with NaOH first] | 6048 mg |
| 100 mM NaCl | 5844 mg |
| 1 mM EDTA (0.5 M stock) | 2000 ul |
| 0.1% W/V CHAPS | 1000 mg |
| 10% Sucrose w/v | 100 g |
| qs d $H_2O$ | 1000 ml |
| 1 mM cysteine | |

Buffer can be made and aliquots taken out for daily use, sterile filter and 4 C storage.

Concentrated Buffer 120% pH 7.2 for Substrates (Concentrations Listed are for Final not 120%)

| | |
|---|---|
| 20 mM PIPES [pH to 7.2 with NaOH first] | 7258 mg |
| 100 mM NaCl | 7013 mg |
| 1 mM EDTA (0.5 M stock) | 2400 ul |
| 0.1% W/V CHAPS | 1200 mg |
| 10% Sucrose w/v | 120 g |
| qs d $H_2O$ | 1000 ml |
| 1 mM cysteine | |

LEHD-AFC (SEQ ID NO: 5) (Caspase 9 Substrate) 25 uM Final Concentration

Enzyme Systems Products catalog #AFC-138

Dissolve 3 mg of LEHD-AFC (SEQ ID NO: 5) in 175 ul of 100% DMSO and freeze at −20 C. This stock is 25 mM Want final concentration of 25 uM in 100 ul. Need concentrated volume of 50 ul therefore need 50 uM for final concentration of 25 uM. Have stock at 25 mM (25000 uM) therefore 25000 uM/50 uM=500. Need approximately 5 ml per plate. 50 uM=1:500 dilution=40 ul 25 mM LEHD-AFC (SEQ ID NO: 5)/20 ml Buffer Caspase-9 Recombinant Human 5 na/ml Final Concentration Positive control PharMingen catalog #66281T Stock enzyme as purchased is 10 ug in 50 ul. This stock is 200 ng/ul Want 5 ng/ml final concentrations of CPP32 enzyme. Final concentrations are in 100 ul but need concentrated enzyme in 40 ul for addition to substrate (50 ul) therefore need (5 ng/ml) (100 ul)=(x ng/ml) (40 ul). Need 12.5 ng/ml stock concentration.

Stock enzyme is 200 ng/ul=200 ug/ml.

(200 ug/ml)/0.0125 ug/ml=16,000 so 1:16,000 dilution of enzyme.

Final Concentration Stock Concentration 5 ng/ml=12.5 ng/ml=1:16,000=2.5 ul CPP 32/40 ml buffer Inhibitor Peptide LEHD-CHO (SEQ ID NO: 5)

Enzyme Systems catalog #AL-010 5 mg MW 502

Storage −20 C dessicated 4 month life (few days in DMSO at −20 C)

10 mM stock in DMSO=5 mg/ml DMSO

The invention claimed is:

1. A method for identifying a compound that modulates Caspase 9 activity, comprising:
   a) contacting a sample containing Caspase 9 with a test compound;
   b) adding a purified kosmotropic agent to the sample containing Caspase 9 such that the sample comprises one or more kosmotropic agents and the final concentration of the kosmotropic agent or agents exceeds 0.3M, and
   c) detecting the activity of Caspase 9, wherein a change in activity indicates a compound which modulates Caspase 9 activity.

2. The method of claim 1, wherein said modulation comprises inhibition of Caspase 9 activity.

3. The method of claim 1, wherein said activity is detected using a binding assay.

4. The method of claim 1, wherein said activity is detected by determining the turnover of a substrate.

5. The method of claim 4, wherein said substrate comprises a peptide.

6. The method of claim 5, wherein the substrate comprises a peptide selected from the group consisting of LEHD (SEQ ID NO: 5), WEHD (SEQ ID NO: 4), DEVD (SEQ ID NO: 1), ZEVD, and YVAD (SEQ ID NO: 7).

7. The method of claim 4, wherein said substrate is a fluorogenic substrate.

8. The method of claim 7, wherein said fluorogenic substrate comprises a labeled peptide selected from the group consisting of LEHD-AMC (SEQ ID NO: 5), WEHD-AMC (SEQ ID NO: 4), DEVD-AMC (SEQ ID NO: 1), ZEVD-AMC, YVAD-AMC (SEQ ID NO: 7), LEHD-AFC (SEQ ID NO: 5), WEHD-AFC (SEQ ID NO: 4), DEVD-AFC (SEQ ID NO: 1), ZEVD-AFC, and YVAD-AFC (SEQ ID NO: 7).

9. The method of claim 1, wherein said sample comprises a cell lysate.

10. The method of claim 1, wherein the agent is a Hofmeister series ion.

11. The method of claim 1, wherein the agent is a sodium salt selected from the group consisting of sulfate, phosphate, acetate, and citrate.

12. The method of claim 1, wherein the agent is an ammonium salt selected from the group consisting of sulfate, phosphate, acetate, and citrate.

13. The method of claim 11 wherein the agent is citrate.

14. The method of claim 12 wherein the agent is citrate.

* * * * *

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial
<220> FEATURE:
<223> OTHER INFORMATION: Substrate

<400> SEQUENCE: 1

Asp Glu Val Asp
1

<210> SEQ ID NO 2
<211> LENGTH: 4
<212> TYPE: PRT
<213> ORGANISM: Artificial
<220> FEATURE:
<223> OTHER INFORMATION: Substrate

<400> SEQUENCE: 2

Ile Glu Thr Asp
1

<210> SEQ ID NO 3
<211> LENGTH: 4
<212> TYPE: PRT
<213> ORGANISM: Artificial
<220> FEATURE:
<223> OTHER INFORMATION: Substrate

<400> SEQUENCE: 3

Leu Glu Glu Asp
1

<210> SEQ ID NO 4
<211> LENGTH: 4
<212> TYPE: PRT
<213> ORGANISM: Artificial
<220> FEATURE:
<223> OTHER INFORMATION: Substrate

<400> SEQUENCE: 4

Trp Glu His Asp
```

```
<210> SEQ ID NO 5
<211> LENGTH: 4
<212> TYPE: PRT
<213> ORGANISM: Artificial
<220> FEATURE:
<223> OTHER INFORMATION: Substrate

<400> SEQUENCE: 5

Leu Glu His Asp
1

<210> SEQ ID NO 6
<211> LENGTH: 4
<212> TYPE: PRT
<213> ORGANISM: Artificial
<220> FEATURE:
<223> OTHER INFORMATION: Substrate

<400> SEQUENCE: 6

Val Glu Ile Asp
1

<210> SEQ ID NO 7
<211> LENGTH: 4
<212> TYPE: PRT
<213> ORGANISM: Artificial
<220> FEATURE:
<223> OTHER INFORMATION: Substrate

<400> SEQUENCE: 7

Tyr Val Ala Asp
1
```